United States Patent
Millet

(10) Patent No.: US 11,058,567 B2
(45) Date of Patent: Jul. 13, 2021

(54) KNEE SUPPORT ORTHOSIS ADAPTED TO A PROLONGED SEATED POSITION

(71) Applicant: MILLET INNOVATION, Loriol sur Drome (FR)

(72) Inventor: Damien Millet, Valence (FR)

(73) Assignee: MILLET INNOVATION, Loriol sur Drome (FR)

( * ) Notice: Subject to any disclaimer, the term of this patent is extended or adjusted under 35 U.S.C. 154(b) by 337 days.

(21) Appl. No.: 16/324,901

(22) PCT Filed: Aug. 23, 2017

(86) PCT No.: PCT/FR2017/052267
§ 371 (c)(1),
(2) Date: Feb. 11, 2019

(87) PCT Pub. No.: WO2018/042108
PCT Pub. Date: Mar. 8, 2018

(65) Prior Publication Data
US 2019/0328566 A1    Oct. 31, 2019

(30) Foreign Application Priority Data

Aug. 29, 2016  (FR) ...................................... 1658001

(51) Int. Cl.
*A61F 5/01*      (2006.01)
*A61F 13/06*     (2006.01)

(52) U.S. Cl.
CPC .................. *A61F 5/0109* (2013.01)

(58) Field of Classification Search
CPC .... A61F 5/0104; A61F 5/0109; A61F 13/061; A61F 2005/0176; A61F 5/0106;
(Continued)

(56) References Cited

U.S. PATENT DOCUMENTS 5,925,010 A    7/1999 Caprio, Jr.
6,279,160 B1*  8/2001 Chen .................... A41D 13/065
                                                 2/24
(Continued)

FOREIGN PATENT DOCUMENTS

DE    92 03 328 U1    4/1992
DE    43 22 028 A1    1/1995
(Continued)

OTHER PUBLICATIONS

Nov. 24, 2017 International Search Report issued in International Patent Application No. PCT/FR2017/052267.

*Primary Examiner* — Tarla R Patel
(74) *Attorney, Agent, or Firm* — Oliff PLC

(57) ABSTRACT

A knee orthosis including: a sleeve made of elastic fabric and configured to exert compressive forces on the knee, proximal and distal anchors for maintaining proximal and distal parts of the sleeve in fixed positions on the lower limb, and a panel including a viscoelastic layer of polymer gel fixed to an inner face of the sleeve, an annular part configured to surround the kneecap, and a distal tab, the viscoelastic layer having an adherence to the skin so, once stretched out longitudinally on the leg, the panel applies forces to the skin for supporting the kneecap, and the sleeve is formed from pieces of fabric including: a front piece supporting the panel, a rear piece and two lateral pieces, the rear and lateral pieces having moduli of elasticity in the axial direction which are respectively less than and greater than the modulus of elasticity of the front piece.

14 Claims, 4 Drawing Sheets

(58) Field of Classification Search
CPC ........ A61F 5/01; A61F 5/0102; A61F 5/0123; A61F 2/38; A61F 2/3886; A61F 2/64
See application file for complete search history.

(56) References Cited

U.S. PATENT DOCUMENTS 6,592,539 B1    7/2003  Einarsson et al.
2002/0095107 A1*  7/2002  Martin ................... A61F 13/06
                                                              602/61

FOREIGN PATENT DOCUMENTS

| EP | 0 229 577 A1 | 7/1987 | | |
|---|---|---|---|---|
| FR | 2 607 384 A1 | 6/1988 | | |
| FR | 2607384 A1 * | 6/1988 | ........... | A61F 13/061 |
| WO | 2014/184459 A1 | 11/2014 | | |

* cited by examiner

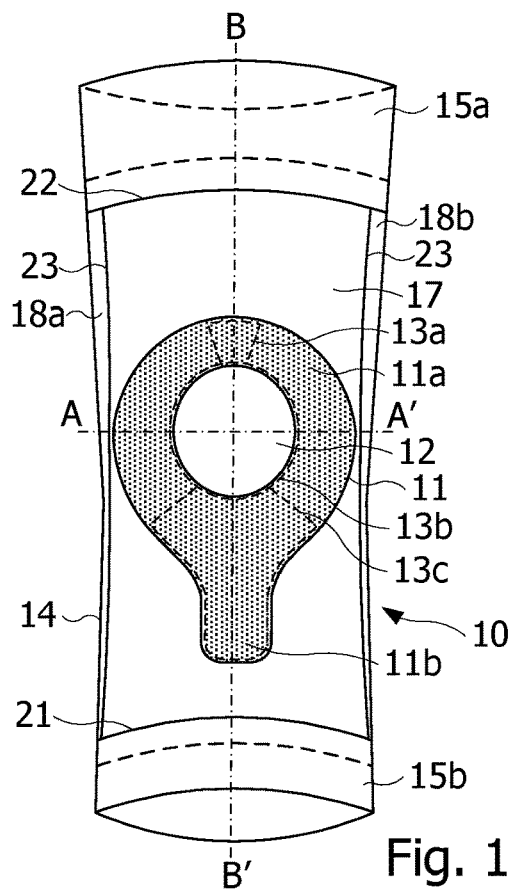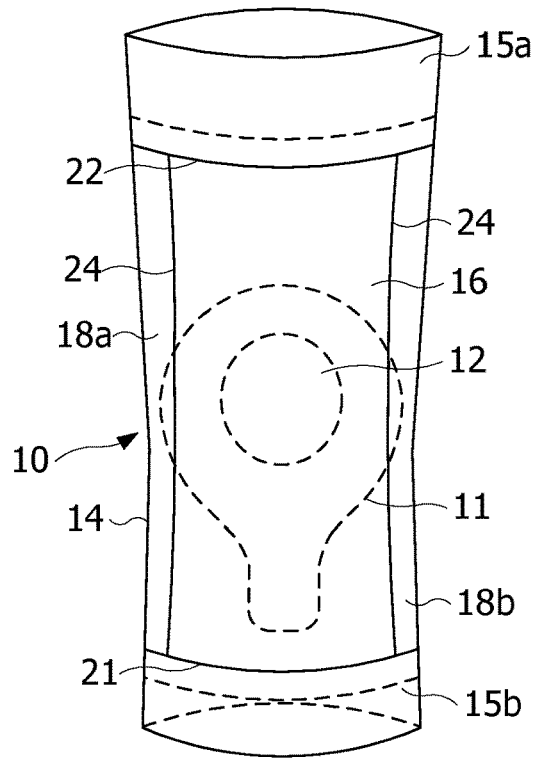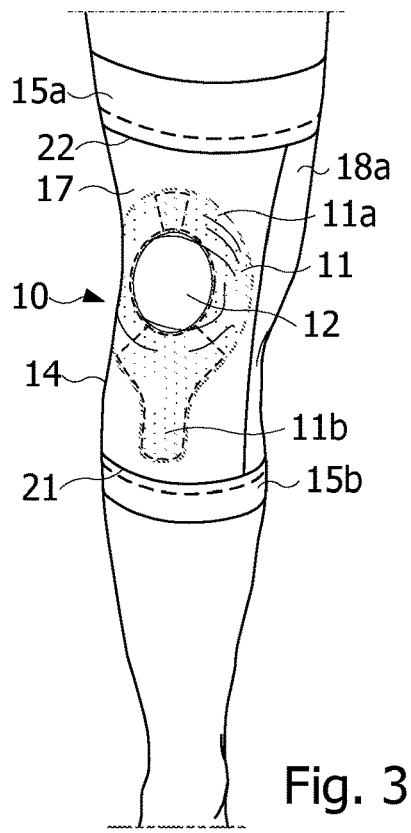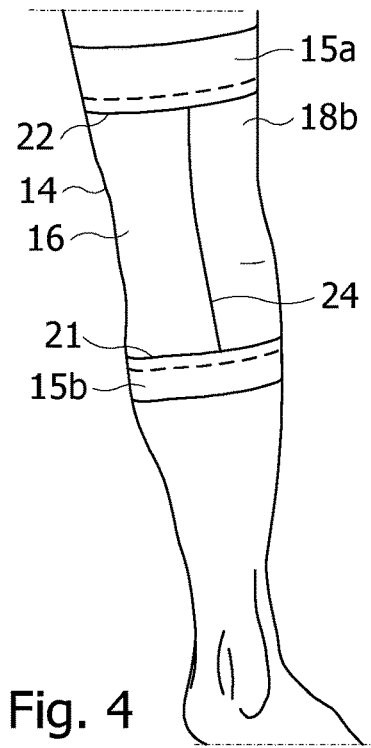

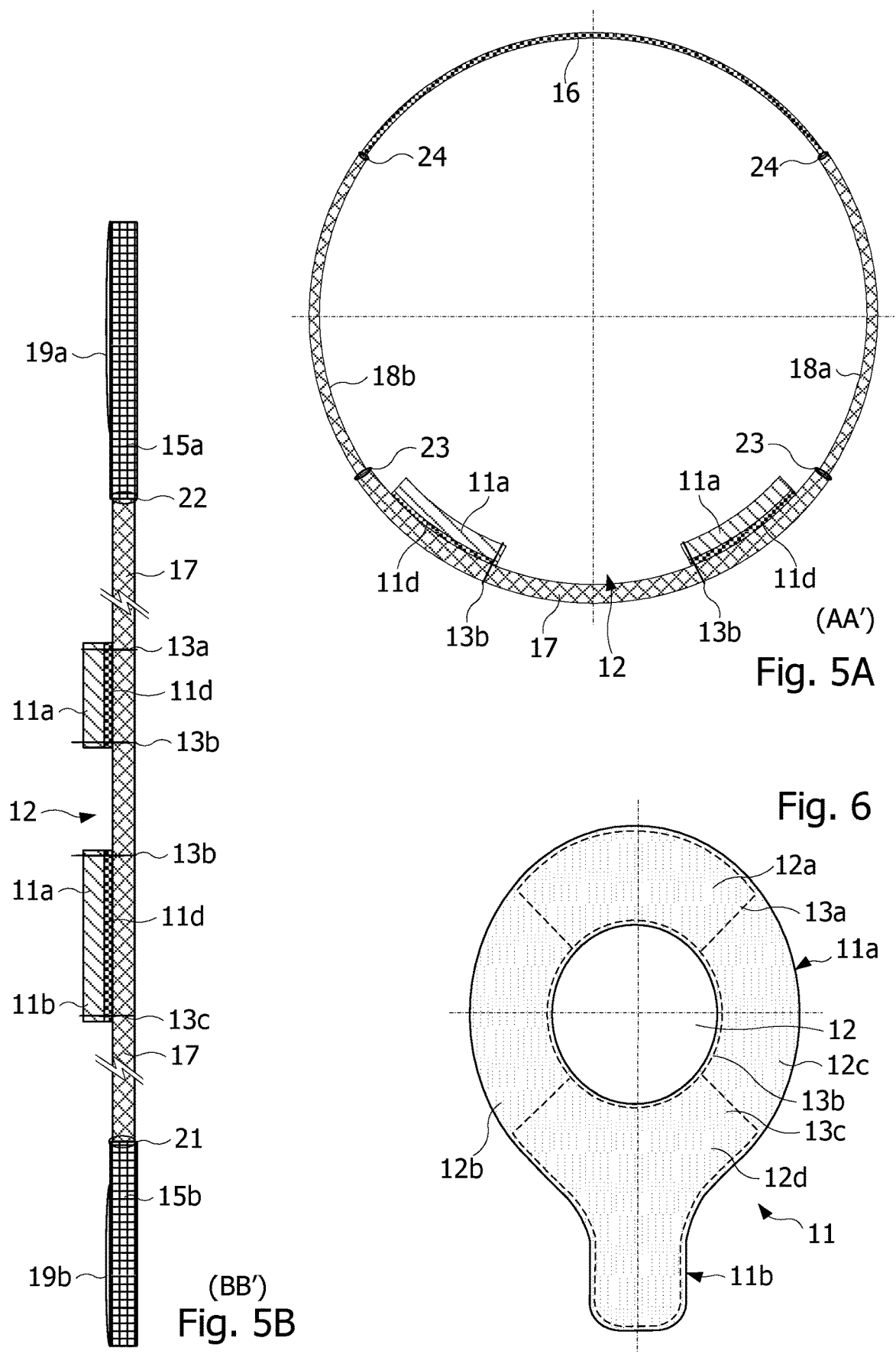

KNEE SUPPORT ORTHOSIS ADAPTED TO A PROLONGED SEATED POSITION

FIELD

The present invention relates to an orthosis for maintaining the knee. The present invention applies in particular, but not exclusively, to supporting the knee without necessarily immobilizing the joint. Such an orthosis can be used to prevent chronic pain, or to relieve a light sprain, or during a recovery of activity following a trauma.

BACKGROUND

There are knee supports or orthoses including "kneecap pelottes" to ensure support of the kneecap, or massage pelottes to massage certain muscles. Such orthoses are described, for example, in US patent applications 2006/0041214, 2010/0036303, and 2011/0160631. The orthoses described in these documents comprise an annular element of foam or silicone, designed to surround the kneecap to support it.

These orthoses have several defects. They are relatively thick and heavy, in particular because they are made using knitting machines that only produce knitted fabrics which cannot be as thin as woven fabrics, i.e. fabrics including a warp thread and a weft thread. Due to the relatively high weight of the knitted fabric, it may be necessary to provide frames to prevent the fabric from collapsing on itself. Because of their relatively high thickness and the presence of frames, they are uncomfortable under pants, or unsuitable for wearing tight pants. During repeated bending of the knee, for example in a competition situation, they tend to slide along the thigh and the leg, especially because of their weight. When the knee is in a flexed condition, the folds that inevitably form in the popliteal fold, at the back of the knee, can overlap to a thickness of several millimeters, which can cause discomfort to the user, or even pain. They often require the use of clamping bands with loops and hooks to ensure sufficient support on the thigh and under the knee.

In patent application WO 2014/184459, the Applicant proposes an orthosis comprising an elastic sleeve, shaped to exert compressive forces on the leg on either side and on the knee, and a pad in a viscoelastic polymer gel attached to an inner face of the sleeve. The pad includes an annular portion shaped to surround the kneecap, and a tab extending from an outer edge of the annular portion, in an axial direction of the sleeve. The pad is configured to adhere to the skin such that, under the effect of the compression forces exerted by the sleeve, when the sleeve is stretched longitudinally, it remains stretched and applies locally supporting forces towards the center of the kneecap, and restoring forces in the axis of the leg.

This orthosis is effective to support the knee during a sports activity. On the other hand, like the other orthoses mentioned above, it cannot be worn all day, especially during long sitting periods, i.e. when the knee joint is maintained flexed at more than 80°. Indeed, in this position, the forces applied by the orthosis to the kneecap can eventually cause unbearable pain. Moreover, the tackiness of the polymer gel under the sleeve applies shearing forces to the skin, which can eventually produce chafing.

There is therefore a need for a knee orthosis adapted to be worn day-long during ordinary activities, including long periods of sitting, without producing undesirable effects.

SUMMARY

Embodiments relate to a knee orthosis comprising: a sleeve of elastic woven fabric, shaped to exert compressive forces on a lower limb on either side and on the knee, a pad comprising a viscoelastic layer, the pad being attached to an inner face of the sleeve so that the viscoelastic layer is in direct contact with the skin of the knee, the pad comprising an annular part shaped to surround the kneecap of the knee, and a distal tab extending from an outer edge of the annular part, in an axial direction of the sleeve, the viscoelastic layer having an adhesion with the skin such that, under the effect of the compressive forces exerted by the sleeve, when the sleeve is stretched longitudinally, the pad stretches and remains stretched by locally applying to the underlying limb portion support forces towards the center of the knee, and restoring forces in the axis of the limb, and proximal and distal anchors for maintaining proximal and distal parts of the sleeve at fixed positions on the lower limb. According to an embodiment, the sleeve is formed from panels of fabric comprising: a front panel to which the pad is attached, a rear panel opposite the front panel, and having a modulus of elasticity in the axial direction of the sleeve, lower than that of the front panel, and two side panels, each attached to a lateral edge of the front panel and to a lateral edge of the rear panel, and having a modulus of elasticity in the axial direction of the sleeve, greater than that of the front panel.

According to an embodiment, the sleeve comprises a proximal sleeve and a distal sleeve, made of elastic fabric, partially covered with a layer adhering to the skin, disposed on an inner face of the proximal and distal sleeves, to come into direct contact with the skin and provide an anchorage to the skin of proximal and distal edges of the sleeve, under the effect of the compressive forces, the proximal sleeve being attached to a proximal edge of each of the front, rear and lateral panels, and the distal sleeve being attached to a distal edge of each of the front, rear and side panels.

According to an embodiment, the orthosis has at least one of the following features: the proximal sleeve has a width between 70 and 80 mm, and the adhering layer formed on the proximal sleeve has a width between 50 and 60 mm; the distal sleeve has a width between 40 and 50 mm, and the adhering layer formed on the distal sleeve has a width between 20 and 30 mm; the adhering layers formed respectively on the proximal and distal sleeves have a surface weight between 18 and 22 μg/cm2; the proximal and distal sleeves are made of an elastic fabric without woolly thread.

According to an embodiment, the pad is attached to the sleeve by a proximal angular sector and a distal angular sector including the tab, the pad having lateral angular sectors not attached to the sleeve.

According to an embodiment, the viscoelastic layer of the pad has a thickness between 0.25 and 0.5 mm, and the proximal, lateral, and distal angular sectors each extend over substantially a quarter of the circumference of the annular part of the pad.

According to an embodiment, the viscoelastic layer of the pad has a thickness between 0.35 and 0.45 mm, and the lateral angular sectors each have an extent 4 to 5 times larger than the proximal angular sector and 1.5 to 2 times larger than the distal angular sector without the tab.

According to an embodiment, the annular part of the pad has, between inner and outer edges, a width in the proximal angular sector, between 2.2 and 2.8 cm, and a width in the lateral angular sectors, between 2.7 and 3.3 cm.

According to an embodiment, the viscoelastic layer of the pad is made of a silicone gel obtained by at least partial polymerization of a mixture of polydimethylsiloxane oils.

According to an embodiment, the pad comprises an elastic fabric layer attached to the viscoelastic layer.

According to an embodiment, the tab of the pad is shaped to cover the tibial tuberosity, the orthosis being adapted to be used indifferently on a right or left lower limb.

According to an embodiment, the orthosis has at least one of the following features: the front panel of the sleeve has a thickness between 0.4 and 0.5 mm; the side panels have a thickness between 0.3 and 0.4 mm; and the rear panel has a thickness between 0.2 and 0.3 mm.

According to an embodiment, the panels forming the sleeve have an elastic modulus under a 40% elongation, along the longitudinal axis of the sleeve, between 1.75 and 2 N for the front panel, between 1.7 N and 3 N for the side panels, and between 1.7 and 1.8 N for the rear panel.

According to an embodiment, the panels forming the sleeve have an elastic modulus under an elongation at 40%, along a transverse axis of the sleeve, between 1.75 and 2 N for the front panel, between 1.7 N and 3 N for the side panels, and between 1.7 and 1.8 N for the rear panel.

According to an embodiment, the front and rear panels extend over approximately one third of the circumference of the sleeve and the side panels extend over about one sixth of the circumference of the sleeve, to within 10%.

BRIEF DESCRIPTION OF DRAWINGS

Other advantages and features will become more clearly apparent from the following description of particular embodiments of the invention provided for exemplary purposes only and represented in the appended drawings, in which:

FIGS. 1 and 2 are front and rear views of a knee orthosis, according to an embodiment, FIGS. 3 and 4 are three-quarter front and rear views of the orthosis of FIG. 1, placed on a right lower limb, FIGS. 5A, 5B are schematic cross-section views of the orthosis according to embodiments, FIG. 5A being a transversal cross-section along a plane AA', and FIG. 5B being a longitudinal cross-section along a plane BB', the planes AA' and BB' being indicated in FIG. 1, FIG. 6 represents a pad of the orthosis, comprising a layer of polymer gel, according to an embodiment.

DESCRIPTION OF EMBODIMENTS

Figure 7A:
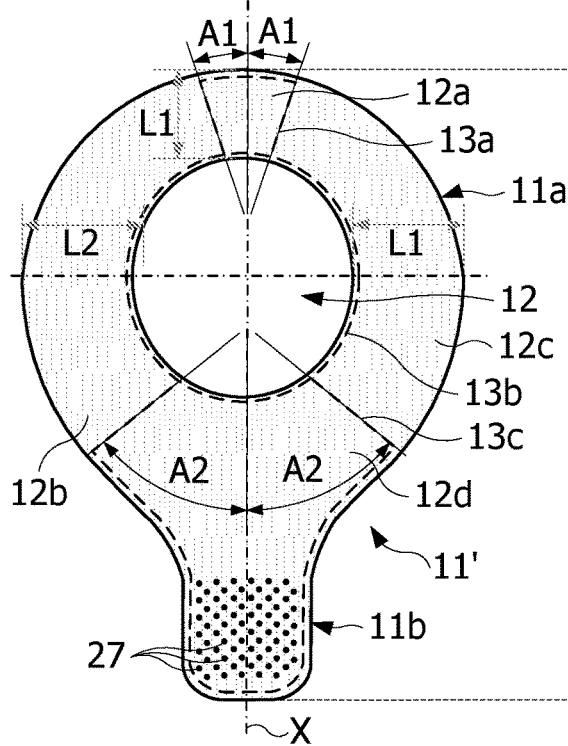
FIGS. 7A, 7B show the pad of the orthosis, according to another embodiment, the pad being represented in two configurations, respectively with the knee extended and the knee flexed.

FIGS. 1 to 4, 5A and 5B show a knee orthosis 10 according to an embodiment, FIGS. 3 and 4 showing the orthosis 10 placed on a right lower limb. FIG. 1 shows the orthosis in an inverted configuration, the visible face being that intended to contact the skin. The orthosis 10 comprises an elastic sleeve 14 and a pad 11 including a layer of a viscoelastic polymer gel, attached to the face of the sleeve 14 configured to contact the skin. The sleeve 14 is shaped to exert compressive forces on the thigh, knee and leg. For this purpose, the sleeve 14 has a tubular shape with a variable diameter in the longitudinal direction of the sleeve, adapted to the diameters of the lower thigh, the knee and the upper calf, so as to obtain the desired compression forces in these different parts of the lower limb. The sleeve 14 is shaped so as to exert compression forces in accordance with the current standards.

According to an embodiment, the sleeve 14 is made of several central panels 17, 18a, 18b, 16 of substantially the same length, a proximal part 15a in the form of a sleeve and a distal part 15b also forming a sleeve. The central panels include a front panel 17 on which the pad 11 is attached, two side panels 18a, 18b, a rear panel 16.

According to an embodiment, the front and back panels 17, 16 extend over approximately one third of the circumference of the sleeve 14, and the side panels 18a, 18b extend over approximately one-sixth of the circumference of the sleeve, to within 10%.

According to an embodiment, the front panel 17 (the most stressed among the panels 17, 18a, 18b, 16 during flexion of the knee) has a modulus of elasticity (Young's modulus) along the axis of the sleeve 14 lower than that of the side panels 18a, 18b, to limit the discomfort that may occur when wearing the orthosis for a long period of sitting. Since the back panel 16 covers a location corresponding to the popliteal fold or cavity of the knee, it is made of an elastic material having a low thickness, for example less than 0.3 mm. This prevents the formation of excess thickness resulting from a superposition of folds, likely to induce discomfort or pain when the knee is flexed while sitting or squatting. Indeed, beyond one millimeter, the excess thickness can induce irritation and chafing. The panel 16 may be attached to the other panels 18a, 18b, 15a, 15b forming the sleeve 14 so as to remain in tension, regardless of the flexion of the knee, without introducing parasitic force play.

According to an embodiment, the parts 15a, 15b hold the sleeve 14 on the thigh and on the calf, to prevent the sleeve 14 from sliding along the leg, either downwards or upwards. For this purpose, the surfaces of the parts 15a, 15b that come into contact with the skin are at least partially covered with a tacky layer 19a, 19b that anchors the proximal and distal edges of the sleeve 14 to the skin. The tacky layers 19a, 19b stick to the skin with greater force than that of the sleeve 14, depending on their intrinsic tackiness, the surface area in contact with the skin and the compressive forces exerted by part 15a, 15b and the tacky layer 19a, 19b. The tacky layers 19a, 19b may be continuous or discontinuous. They may thus be made for instance in the form of a layer, for example deposited by coating, or be made in the form of studs. The layer and the studs may for example be made of a polymer gel such as a silicone gel, chosen for its tackiness property with the skin. The width of each of the tacky layers 19a, 19b and the compression effect exerted on the thigh or the calf by the parts 15a, 15b can be adapted to the desired degree of holding of the sleeve 14 on the leg while avoiding excessive compressive forces on the limb. Thus, the skin adhesion forces that anchor the top and bottom of the orthosis on the skin can be set at a higher value than the forces involved in bending the leg, taking into account the elasticity of the panel 17, to prevent sliding between the tacky layers 19a, 19b and the skin, that eventually causes chafing. The tacky layers 19a, 19b may be made of a polymer gel such as a silicone gel obtained by polymerization of a mixture of polydimethylsiloxane oils.

The panels 17, 18a, 18b, 16, 15a and 15b can be made of elastic fabrics assembled to form the sleeve 14, for example through seams 21, 22, 23, 24. The front panel 17 is attached to the side panels 18a, 18b by seams 23. The rear panel 16 is attached to the side panels 18a, 18b by seams 24. The proximal part 15a is attached to the sleeve 14 (including the panels 17, 18a, 18b, 16) by a seam 22. The distal part 15b is attached to the sleeve 14 by a seam 21. According to an embodiment, the panels 17, 18a, 18b and 16 forming the sleeve 14 are assembled edge to edge to prevent increased thickness.

The knee support structure that has just been described, including a four-part central sleeve 14, 18a, 18b, 16, and proximal and distal sleeves 15a, 15b, has the advantages of exerting forces locally adapted to the area of application, and of being simple to manufacture. In particular, the use of different fabric panels to make the sleeve 14 makes it possible to adjust the stiffness of each panel of the sleeve 14 around the calf and the thigh, as a function of the elongation of that panel when the knee is flexed. Thus, the panel 17 elongates the most when the knee is flexed, while the panel 16 is not stressed during this movement.

FIG. 6 shows the pad 11, according to an embodiment. The pad 11 includes an annular portion 11a with a central opening 12, and a tab 11b extending from an outer edge of the annular portion. In FIGS. 1 and 3, the pad is attached to the inner face of the sleeve 14 at a location where the annular portion 11a can surround the kneecap, and the tongue 11b can cover the anterior tibial tuberosity (FIG. 3). The tab 11b therefore extends in a distal direction of the sleeve 14. The opening 12 has a circular or elliptical shape with dimensions slightly smaller than those of the kneecap. The annular portion 11a has a width (between its inner and outer edges) ranging from 2 to 4 cm. The tab 11b has dimensions slightly greater than those of the tibial tuberosity. The tab 11b may have a width sufficient to avoid making different orthoses for the left and right knees, despite the fact that the anterior tibial tuberosity is not central with respect to a longitudinal axis of the leg passing through the center of the kneecap.

The pad 11 has an adhesion with the skin such that, under the effect of the compressive forces exerted by the sleeve 14, when the sleeve is stretched longitudinally, it remains stretched and locally applies to the skin tensile forces parallel to the surface of the skin, towards the center of the annular part.

The pad 11 may be attached to the sleeve 14 (on the panel 17) by seams. In the example of FIGS. 1, 3 and 6, the pad 11 is attached by seams 13a, 13b 13c. The seam 13a is formed along a proximal portion of the outer edge of the annular part 11a, on a proximal angular sector of the annular part 11a. The ends of the seam 13a may join the inner edge of the annular part, but this is not essential. The seam 13b is formed along the entire inner edge of the annular part 11a. The seam 13c is formed along a distal portion of the outer edge of the pad 11 including the edge of the tab 11b, on a distal angular sector of the annular part 11a. The ends of the seam 13c can join the inner edge of the annular part, but this is not essential. In other words, the seams 13a and 13c divide the pad from the annular portion 11a into four sectors 12a to 12d (FIG. 6), namely a proximal sector 12a attached to the panel 17, a distal sector 12d attached to the panel 17, including the tab 11b, and two lateral sectors 12b, 12c, not attached. The seams 13a, 13c are made along the edges of the proximal sector 12a and the distal sector 12d. The outer edges of the lateral sectors 12b, 12c are therefore left free. Note that the seam 13b attaching the inner edge of the annular part 11a to the sleeve 14 simply serves to prevent gaping and can be omitted totally, or partially by including the portions located on the proximal and distal sectors 12a, 12d.

Instead of being sewn, the proximal and distal sectors 12a, 12d of the pad 11 may be attached to the sleeve 14 by a layer of adhesive, the lateral sectors 12b, 12c not being attached to the sleeve 14.

FIGS. 5A, 5B show the orthosis 10 and the pad 11 assembled to the orthosis. The pad 11 includes a piece of elastic woven fabric 11d attached to one side of the polymer gel layer of the pad 11, without closing the opening 12 of the annular part 11a. The assembly of the pad 11 and the fabric piece 11d can be performed, for example, by gluing. The ensemble of the pad 11 including the piece of fabric 11d and the layer of polymer gel can then be sewn by the seams 13a, 13b, 13c to panel 17 of the sleeve 14. The seams 13a and 13c can be omitted by gluing the piece of fabric 11d (which is glued to the pad) to panel 17, by a layer of glue spread over the proximal and distal annular sectors 12a, 12d (delimited in FIG. 6 by the seams 13a and 13c). The piece of fabric 11d has a thickness of less than 0.5 mm, for example 0.4 mm, and can be made for example in the same fabric as the rear panel 16.

The hardness and thickness of the pad 11 may be chosen to allow sewing of the entire pad 11 (with the piece of fabric 11d). Furthermore, the tackiness of the polymer gel layer of the pad 11 may be chosen to prevent the pad from sliding on the skin, taking into account the compressive forces exerted by the sleeve 14 on the knee.

According to an embodiment illustrated in FIG. 6, the annular sectors 12a to 12d delimited by the seams 13a and 13c each extend about a quarter (within 10%) of the circumference of the annular part 11a, and the pad has a stiffness sufficiently low to allow comfortable wearing of the orthosis for long periods of sitting.

According to an embodiment, the polymer gel layer of the pad 11 is formed of a silicone gel obtained by at least partial polymerization of a mixture of silicone oils such as polydimethylsiloxane oils. Such a mixture can produce a variety of silicone gels having different properties including hardness and tackiness, depending on the respective proportions of the silicone oils of the mixture, which define the degree of polymerization of the mixture. Thus, by adjusting these proportions, it is possible to obtain a more or less hard and more or less tacky viscoelastic gel. The adjustment of the hardness of the pad 11 may account for the elasticity and wear resistance requirements, bearing in mind that the pad will be highly stressed mechanically, and the hardness requirement, especially in the case where the wafer is sewn. Indeed, if the viscoelastic gel is too soft, it will tend to foul the needles used for making the seams. Note that the elasticity of the pad 11 also depends on its shape and its dimensions, and in particular its thickness. Thus, given its stiffness, the polymer gel layer of the pad 11 may have a thickness between 0.25 and 0.5 mm.

The orthosis may be fitted on a leg by pulling it over the foot by the upper edge of the sleeve 14, namely the part 15a, until the pad 11 is placed over the kneecap (FIG. 3). The natural stiffness of the sleeve sets the elongation of the sleeve, which is much lower than the elastic limit of the fabric forming the sleeve. It turns out that the elongation of the portion of the sleeve covering the thigh, when flexing the knee at 90°, remains less than 20% in the zone of the sleeve where traction is maximum, and remains less than 10% at 4 cm from this area towards the part 15a. This elongation is much less than the maximum elongation of the fabric forming the sleeve. In these conditions, the alternating folding of the knee during walking or running does not significantly affect the holding of the sleeve 14 on the thigh, ensured by the band 15a. As a result, the parts 15a, 15b are sufficient to prevent the orthosis from slipping.

It can be seen that the elastic stress in the fabric of the sleeve 14 is maximum just above the kneecap and decreases towards the top of the thigh. The sleeve 14 can therefore be provided with a sufficient length between the location of the pad 11 and its proximal edge, so as to place the part 15a in an area of the thigh where the elastic stress in the sleeve 14 is relatively low (where the skin stretches little). According to an embodiment, the part 15a may be wider than the part 15b, typically twice the width of the part 15b.

According to an embodiment, the sleeve 14 may be made to cover the thigh over a length of 18 to 28 cm (within 10%) from the axis of the kneecap.

The panels 17, 18a, 18b, 16, 15a and 15b can be made from woven fabrics that are elastic in two perpendicular directions, for example along the warp and weft of the fabric, the warp of these panels being along the axis of the thigh or leg and the weft along a perpendicular direction. Thus, the fabric forming the panel 17 of the sleeve 14 may have a thickness between 0.4 and 0.5 mm, for example 0.42 mm, a maximum elongation (depending on the warp and the weft of the fabric) between 80 and 90%, for example 85%, and a modulus of elasticity (Young's modulus) at 40% elongation between 1.75 and 2 N, for example 1.8 N for the weft and 1.95 N for the warp. The fabric forming the side panels 18a, 18b may have a thickness between 0.3 and 0.4 mm, for example 0.38 mm, a maximum elongation (depending on the warp and the weft of the fabric) between 90 and 100%, for example 92% for the warp and 99% for the weft, and a modulus of elasticity at 40% between 1.7 N and 3 N, for example 2 N for the weft and 2.7 N for the warp. The fabric forming the rear panel 16 may have a thickness between 0.2 and 0.3 mm, for example 0.27 mm, a maximum elongation (depending on the warp and the weft of the fabric) between 65 and 75%, for example 70% for the warp and 67% for the weft, and a modulus of elasticity at 40% between 1.7 and 1.8 N, for example 1.74 N for the warp and 1.73 N for the weft.

The fabric forming the proximal and distal parts 15a, 15b may have a thickness between 0.5 and 0.7 mm, for example 0.67 mm. The parts 15a, 15b may be partially covered by a tacky layer 19a, 19b having a surface weight between 18 and 22 µg/cm2, for example 20 µg/cm2. The tacky layers 19a, 19b may thus have a thickness between 0.15 and 0.25 mm. It is possible to achieve such low weight values for the tacky layers 19a, 19b by using a fabric woven without woolly thread to make the parts 15a, 15b. The fabric forming the proximal part 15a may have a width (along the axis of the leg) of 70 to 80 mm, for example 77 mm. The layer 19a may have a width (along the axis of the leg) of 50 to 60 mm, for example 53 mm. The fabric forming the proximal part 15a may have a modulus of elasticity at 40% between 4 and 5 N, for example 4.5 N without the tacky coating, and between 6 and 7.5 N, for example 6.2 N with the tacky coating 19a. The fabric forming the distal part 15b may have a width (along the axis of the leg) of 40 to 50 mm, for example 45 mm. The layer 19b may have a width (along the axis of the leg) between 20 and 30 mm, for example 25 mm. The fabric forming the distal part 15b may have a modulus of elasticity at 40% between 2 and 3 N, for example 2.6 N without the tacky coating, and between 3 and 4 N, for example 3.4 N with the tacky coating 19b. All the above numerical characteristics of panels 17, 18a, 18b, 16, 15a and 15b are defined to within 5%.

Figure 7B:
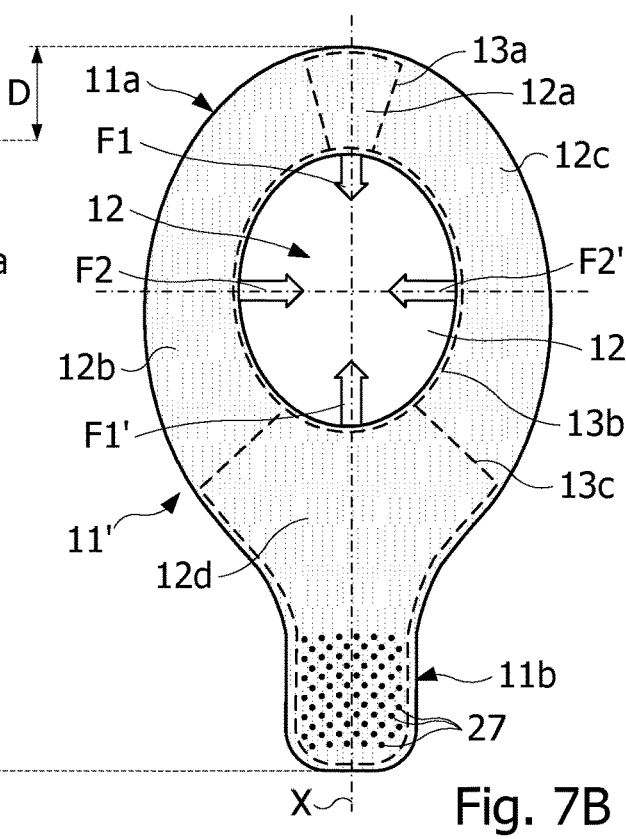

FIGS. 7A, 7B show a pad 11' according to another embodiment. FIGS. 7A, 7B use the same reference numerals as in FIG. 6 to denote same elements. The pad 11' differs from the pad 11 by a variable width of the annular part 11a, and by angular sectors 12a to 12d having different extents. Thus, the annular part 11a of the pad 11' has, between its inner and outer edges, a width L1 in the angular sector 12a between 2.2 and 2.8 cm, for example 2.5 cm, and a width L2 in the angular sectors 12b and 12c, between 2.7 and 3.3 cm, for example 3 cm. The lateral sectors 12b, 12c have an extent 4 to 5 times greater than the proximal sector 12a. For example, the proximal angular sector 12a extends over an angle A1, having its vertex at the center or a focal point of the opening 12, of about 10 to 25°, for example between 13 and 20°, on either side of a longitudinal axis X of the pad 11. The lateral sectors 12b, 12c have an extent between 1.5 and 2 times that of the distal angular sector 12d without the tab 11b. For example, the distal angular sector 12d extends over an angle A2, having its vertex at the center or a focal point of the opening 12, of about 40 to 58°, for example between 52 and 54°, on either side of the longitudinal axis X. The pad 11' may have a thickness between 0.6 and 1 mm, for example. These dimensions are defined to within 5%. These configurations make it possible to lengthen the stretchable part of the pad, namely the lateral angular sectors 12b, 12c, and thus to increase the elasticity (the stretching capacity under a same stretching force) of these angular sectors, without having to decrease the thickness of the pad. Indeed, the assembly of the pad on the sleeve 14 by seams can cause resilience problems if the thickness of the pad is too low. Thus, the forces exerted by the pad 11' on the kneecap are lower, despite a greater thickness of the pad (relative to the pad 11), which also allows longer periods of sitting without discomfort.

FIGS. 7A, 7B show the pad 11' respectively in non-stretched and stretched configurations, for example when the orthosis is in place on a lower limb, respectively, with the knee extended and the knee flexed. In non-stretched configuration, the opening 12 of the wafer 11' is substantially circular or elliptical, adapted to the shape of the kneecap. The tab 11b forms an anchor point on the skin, obtained by the conjunction of the compressive force exerted by the sleeve 14 on the pad 11', the surface of the pad and in particular of the tab 11b, and the tackiness of the polymer gel layer of the pad. The band 15a is an anchor point of the sleeve 14 on the thigh, and the band 15b is an anchor point of the sleeve on the calf.

During stretching of the sleeve 14, when the knee is flexed, part of the stretching is transmitted to the pad 11' because of its adhesion to the skin, the anchoring of the sleeve 14 by the bands 15a, 15b, and additional anchoring of the pad 11' resulting in particular from the connection of the pad to the kneecap through the annular part 11a. This results in an elongation D of the pad 11' and in particular of the annular part 11a. The elongation D causes an elastic deformation of the pad 11', causing in particular a deformation of the opening 12 which expands in the longitudinal direction of the sleeve 14 and compresses in the transverse direction of the sleeve 14. This results in traction forces parallel to the surface of the skin exerted by the pad on the skin and on the volume of the limb surrounded by the pad. These forces include opposing longitudinal forces F1, F1' oriented toward the center of the opening 12 and opposing transverse forces F2, F2', also oriented towards the center of the opening 12. The forces F2, F2' maintain the kneecap and avoid its lateral discharge.

The forces F1, F1' participate in unrolling each step while walking or running. Thus, while walking or running, the annular part 11a stretches during an active phase when the foot is placed on the ground, while the inertia of the body participates in the flexion of the knee. During a passive phase where the foot no longer rests on the ground and the lower limb is stretched forward to take a new step, the annular part 11a resumes its non-stretched configuration and thus restores the stored elastic energy to the leg. Even if the forces F2, F2' are relatively weak, they are sufficient to ensure some support of the kneecap and relieve the joint by providing the sensation that the joint is supported (proprioceptive effect of the orthosis). As for the forces F1 and F1', their presence is perceived through the musculotendinous system to which they apply.

It should be noted that the pad 11 (FIG. 6) behaves in the same manner (previously described) as the pad 11', the forces F1, F1', F2, F2' also appearing when the pad 11 is stretched.

Figure 8:
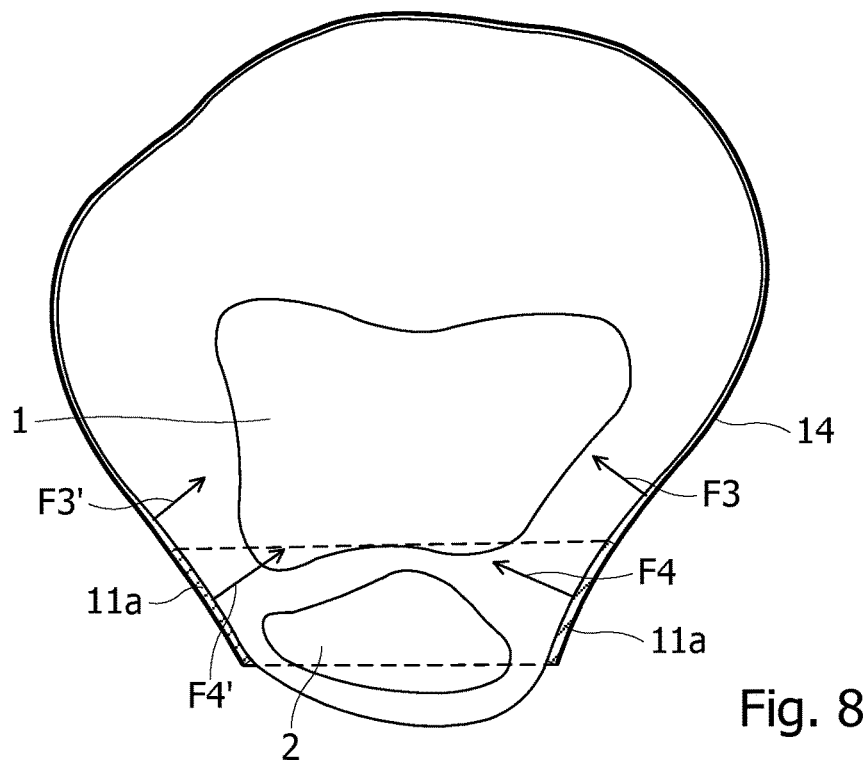
FIG. 8 is a cross-section view of the right knee, wearing the orthosis.

FIG. 8 shows a cross section of the right knee and the orthosis surrounding it. It can be observed that the annular part 11a assumes a substantially frustoconical concave shape, enveloping the lateral right, left, lower and upper portions of the kneecap 2. FIG. 8 also shows by arrows the forces F3, F3', F4, F4' exerted by the orthosis on the lateral edges of the kneecap 2, these forces being exerted perpendicular to the surface of the sleeve 14 and of the annular part 11a of the pad 11, 11'. The forces F3, F3' exerted by the sleeve 14 are directed towards the center of the knee, and the forces F4, F4' exerted by the annular part 11a of the pad 11 are directed substantially parallel to the surface of the interface between the kneecap 2 and the femur 1. The orthosis thus ensures lateral support of the kneecap 2, in particular when the knee is in extension or at the beginning of a flexion movement, that is to say in positions where the tissues which surround it are the slackest.

It should be noted that the longitudinal expansion of the pad 11', in particular of the annular part 11a, especially in the seated position, is partly facilitated by the absence of seams on the outer edge of the lateral sectors 12b, 12c of the annular part 11a, which are relatively extended, and by the smaller width L1 of the angular sector 12a of the annular part 11a. It should also be noted that the sleeve 14, in particular the front panel 17, may have a greater longitudinal stretching capacity than the elongations that occur in the seated position, in order to avoid sliding of the proximal and/or distal edges of the sleeve. along the thigh or calf. If the longitudinal stretching capacity of the pad 11, 11' and the panel 17 is increased, the compressive forces exerted by the parts 15a, 15b can be reduced, which helps to limit the discomfort resulting from wearing the orthosis for long periods.

These configurations make it possible to obtain a knee orthosis weighing less than 45 g (in comparison with the prior art orthoses which presently weigh more than 150 g), while ensuring an effective support of the kneecap compatible with a prolonged use during a whole day, and with common dynamic activities (outside sports activities soliciting the knee) or static activities, where the knee can remain folded up to 110 degrees for long periods.

According to an embodiment, the tab 11b has studs 27 to increase its adhesion to the skin (FIGS. 7A, 7B). These studs may be formed, for example, during the manufacture by molding of the pad 11, 11'.

Figure 9A:
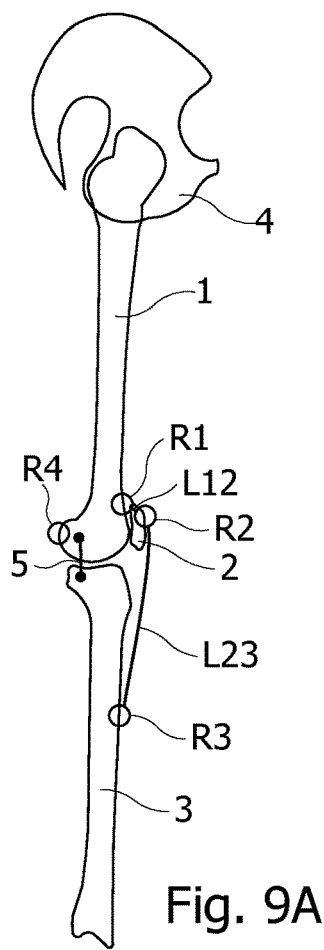
FIGS. 9A, 9B, 9C are sagittal cross-sections of the bones of a right lower limb (iliac bone, femur, kneecap, tibia), with the knee respectively extended, flexed at 90°, and flexed at 90° wearing the orthosis.
Figure 9B:
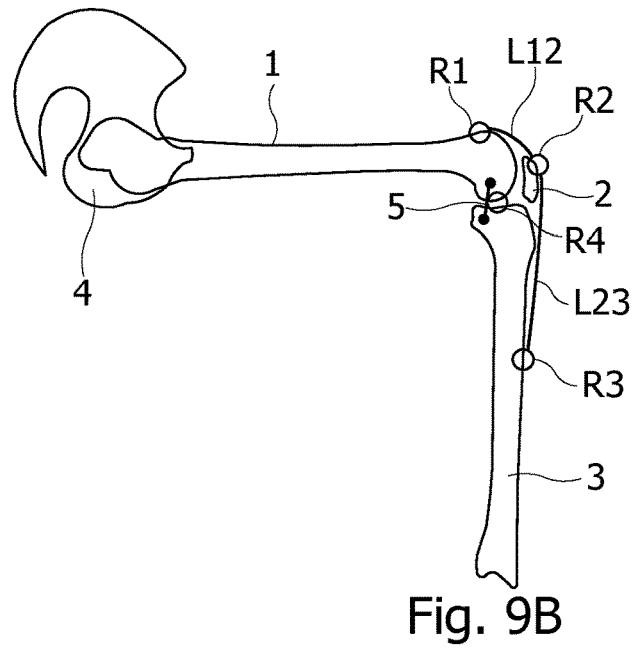
Figure 9C:
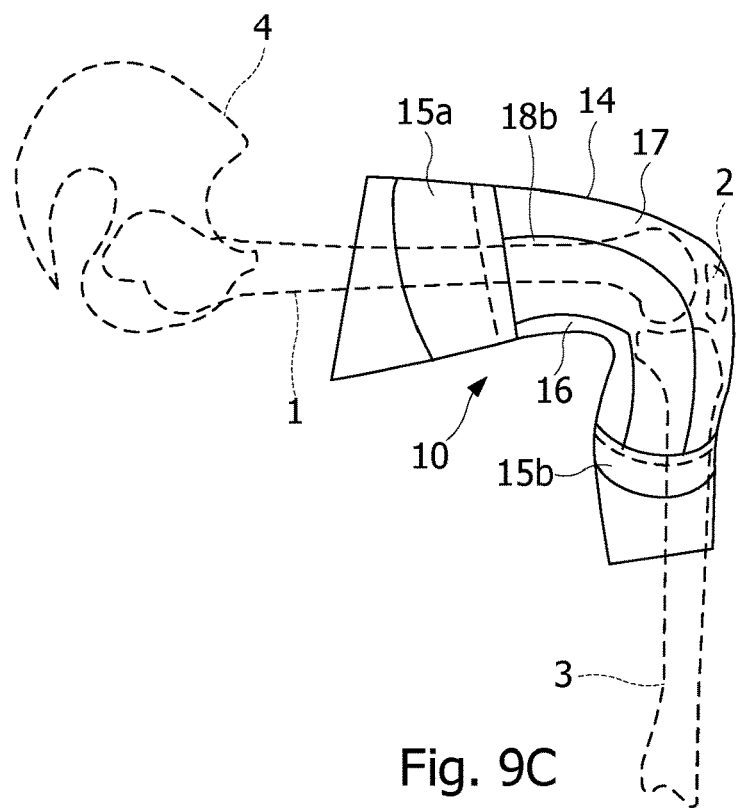

FIGS. 9A, 9B show the bones of a lower limb and pelvis in sagittal section (iliac bone 4, femur 1, tibia 3 and kneecap 2), in configurations where the knee is extended and the knee is flexed at about 90°. FIG. 9C shows the flexed knee configuration superimposed on the part of the leg equipped with the orthosis 10. FIGS. 9A, 9B symbolize, by circles, anterior reference points R1, R2, R3 and a posterior reference point R4 on the bones, and by lines L12, L23, tissues (muscles, tendons) connecting the reference points R1, R2 and R2, R3. The points R1 and R4 are respectively located on the anterior (condyle) and posterior edges of the femur 4.

Point R2 is located on the kneecap 2. The point R3 is located in a distal position on the tibia 3. FIGS. 9A, 9B also show the inner and outer lateral ligaments 5 which are stretched when the knee is extended. During a flexion phase of the knee, the orthosis exerts a force F contributing to support the kneecap 2 and laterally stabilize the knee.

FIGS. 9A, 9B show that the anterior links L12 between the points R1 and R2 and L23 between the points R2 and R3 are stretched between the extended and flexed knee configurations. As a result, in the flexed configuration (in particular in the seated position), the panel 17 of the sleeve 14 remains stretched, generating a permanent tension between the pad 11 and the proximal part 15a, as well as between the pad 11 and the distal part 15b. It turns out that this permanent tension induces shear forces at the interface between the sleeves 15a, 15b and the skin.

The characteristics of elasticity and adhesion of the sleeves 15a, 15b, and in particular the sleeve 15a, are linked to the elasticity of the part of the sleeve 14 most stressed during knee flexion, namely the panel 17. If the sleeves 15a, 15b adhere insufficiently to the skin, the extension force applied to the panel 17 during the flexion of the knee, and transmitted to the sleeves 15a, causes a sliding of the sleeves, which is not satisfactory because the sleeve 14 will form folds and thus no longer play its role of supporting the kneecap. Conversely, if the sleeves 15a, 15b strongly adhere to the skin, and if the panel 17 has too high a stiffness, the extension force applied to the panel 17, and transmitted to the sleeves 15a, 15b in the form tensile forces, causes the sleeves to solicit the underlying skin beyond its mechanical shear strength. Therefore, the stiffness of the panel 17 is adapted to not solicit the skin under the sleeves 15a, 15b beyond its mechanical shear strength, and the tension and the tackiness of the sleeves 15a, 15b around the leg are selected at values such that the sleeves 15a, 15b are not likely to slip during flexion of the knee, taking into account the tensile force exerted on the sleeves 15a, 15b by the sleeve 14, and in particular by the panel 17.

It will be apparent to those skilled in the art that the present invention may be subject to various alternative embodiments and various applications. In particular, the invention is not limited to an orthosis including the sleeves 15a, 15b. Indeed, the sleeves 15a, 15b may be partially or completely removed, replacing the sleeve 14 by a garment such as pedal-pushers or tights (for the knee), covering the pelvis and at least one lower limb of the user, to be maintained by the orthosis. The distal sleeve 15b may be removed by adjusting the shape of the garment, using the tapered shape of the calf in the vicinity of the ankle. It is important merely that the orthosis has proximal and distal anchors to maintain proximal and distal portions of the sleeve 14 at fixed positions on the lower limb.

The invention claimed is:
1. A knee orthosis comprising:
  a sleeve of elastic woven fabric, shaped to exert compressive forces on a lower limb on either side and on a knee,
  a pad comprising a viscoelastic layer, the pad being attached to an inner face of the sleeve so that the viscoelastic layer is in direct contact with a skin of the knee, the pad comprising an annular part shaped to surround a kneecap of the knee, and a distal tab extending from an outer edge of the annular part, in an axial direction of the sleeve, the viscoelastic layer having an adhesion with the skin such that, under an effect of compressive forces exerted by the sleeve, when the sleeve is stretched longitudinally, the pad stretches and remains stretched by locally applying to an underlying limb portion support forces towards a center of the knee, and restoring forces in an axis of the limb, and proximal and distal anchors for maintaining proximal and distal parts of the sleeve at fixed positions on the lower limb, wherein the sleeve is formed from panels of fabric comprising:

a front panel to which the pad is attached, a rear panel opposite the front panel, and having a modulus of elasticity in the axial direction of the sleeve, lower than a modulus of elasticity in the axial direction of the sleeve of the front panel, and two side panels, each attached to a lateral edge of the front panel and to a lateral edge of the rear panel, and having a modulus of elasticity in the axial direction of the sleeve, greater than the modulus of elasticity in the axial direction of the sleeve of the front panel.

2. The orthosis according to claim 1, wherein the sleeve comprises a proximal sleeve and a distal sleeve, made of elastic fabric, partially covered with an adhering layer for adhering to the skin, disposed on an inner face of the proximal and distal sleeves, to come into direct contact with the skin and provide an anchorage to the skin of proximal and distal edges of the sleeve, under the effect of the compressive forces, the proximal sleeve being attached to a proximal edge of each of the front, rear and lateral panels, and the distal sleeve being attached to a distal edge of each of the front, rear and side panels.

3. The orthosis according to claim 2, having at least one of the following features:

the proximal sleeve has a width between 70 and 80 mm, and the adhering layer formed on the proximal sleeve has a width between 50 and 60 mm, the distal sleeve has a width between 40 and 50 mm, and the adhering layer formed on the distal sleeve has a width between 20 and 30 mm, the adhering layers formed respectively on the proximal and distal sleeves have a surface weight between 18 and 22 µg/cm$^2$, the proximal and distal sleeves are made of an elastic fabric without woolly thread.

4. The orthosis according to claim 1, wherein the pad is attached to the sleeve by a proximal angular sector and a distal angular sector including the distal tab, the pad having lateral angular sectors not attached to the sleeve.

5. The orthosis according to claim 4, wherein the viscoelastic layer of the pad has a thickness between 0.25 and 0.5 mm, and the proximal, lateral, and distal angular sectors each extend over substantially a quarter of a circumference of the annular part of the pad.

6. The orthosis according to claim 4, wherein the viscoelastic layer of the pad has a thickness between 0.35 and 0.45 mm, and the lateral angular sectors each have an extent 4 to 5 times larger than the proximal angular sector and 1.5 to 2 times larger than the distal angular sector without the distal tab.

7. The orthosis according to claim 6, wherein the annular part of the pad has, between inner and outer edges, a width in the proximal angular sector, between 2.2 and 2.8 cm, and a width in the lateral angular sectors, between 2.7 and 3.3 cm.

8. The orthosis according to claim 1, wherein the viscoelastic layer of the pad is made of a silicone gel obtained by at least partial polymerization of a mixture of polydimethylsiloxane oils.

9. The orthosis according to claim 1, wherein the pad comprises an elastic fabric layer attached to the viscoelastic layer.

10. The orthosis according to claim 1, wherein the distal tab of the pad is shaped to cover a tibial tuberosity, the orthosis being adapted to be used indifferently on a right or left lower limb.

11. The orthosis according to claim 1, having at least one of the following features:

the front panel of the sleeve has a thickness between 0.4 and 0.5 mm, the side panels have a thickness between 0.3 and 0.4 mm, and the rear panel has a thickness between 0.2 and 0.3 mm.

12. The orthosis according to claim 1, wherein the panels forming the sleeve have an elastic modulus under a 40% elongation, along a longitudinal axis of the sleeve, between 1.75 and 2 N for the front panel, between 1.7 N and 3 N for the side panels, and between 1.7 and 1.8 N for the rear panel.

13. The orthosis according to claim 1, wherein the panels forming the sleeve have an elastic modulus under an elongation at 40%, along a transverse axis of the sleeve, between 1.75 and 2 N for the front panel, between 1.7 N and 3 N for the side panels, and between 1.7 and 1.8 N for the rear panel.

14. The orthosis according to claim 1, wherein the front and rear panels extend over approximately one third of a circumference of the sleeve and the side panels extend over about one sixth of the circumference of the sleeve, to within 10%.

* * * * *